United States Patent [19]

Czaja et al.

[11] 4,233,457
[45] Nov. 11, 1980

[54] PROCESS FOR PREPARING INDENYL ACETIC ACIDS

[75] Inventors: Robert F. Czaja, Scotch Plains; Edward J. J. Grabowski, Westfield, both of N.J.

[73] Assignee: Merck & Co., Inc., Rahway, N.J.

[21] Appl. No.: 39,709

[22] Filed: May 17, 1979

[51] Int. Cl.³ ............................................ C07C 147/14
[52] U.S. Cl. .................................... 562/428; 560/105

[58] Field of Search ........................ 562/428; 560/105

*Primary Examiner*—Paul J. Killos
*Attorney, Agent, or Firm*—Thomas E. Arther; Mario A. Monaco; Rudolph J. Anderson, Jr.

[57] ABSTRACT

This invention relates to an improved process for preparing 5-fluoro-2-methyl-1-(p-methylsulfinylbenzylidene)-3-indenyl acetic acid.

4 Claims, No Drawings

PROCESS FOR PREPARING INDENYL ACETIC ACIDS

BACKGROUND OF THE INVENTION

5-Fluoro-2-methyl-1-(p-methylsulfinylbenzylidene)-3-indenyl acetic acid is a known compound having antiinflammatory activity as disclosed in U.S. Pat. No. 3,654,349. The compound has been prepared by a number of methods as disclosed in the above-mentioned patent as well as U.S. Pat. No. 3,870,753. In one of the methods described in U.S. Pat. No. 3,870,753, 5-fluoro-2-methyl-1-(p-methylthiobenzyl) indenylidene-3-acetic acid is isomerized in excess aqueous acid to produce 5-fluoro-2-methyl-1-(p-methylthiobenzylidene) indenyl-3-acetic acid, followed by oxidation to produce the desired compound.

It is an object of this invention to provide an improved method for isomerizing 5-fluoro-2-methyl-1-(p-methylthiobenzyl) indenylidene-3-acetic acid. It is a further object to prepare the desired compound via an improved process which is advantageous over the process described above.

It is a further object of the present invention to provide an improved method for preparing 5-fluoro-2-methyl-1-(p-methylsulfinylbenzylidene)-3-indenyl acetic acid by utilizing the improved isomerization step followed by oxidation to the desired product.

DESCRIPTION OF THE INVENTION

In accordance with one aspect of this invention, it is now been found that the combination of reaction steps disclosed in U.S. Pat. No. 3,870,753 can be substantially improved by the method of carrying out the isomerization step by a previously undisclosed method with substantial increase in yield and substantial economic advantages. In the presently improved method of carrying out the isomerization step, the reaction is conducted in the presence of a minimal amount of anhydrous hydrogen bromide under substantially anhydrous conditions, preferably utilizing a halogenated hydrocarbon, as for example, ethylene dichloride, in a sealed reaction vessel.

The prior process utilized large excesses of aqueous acetic acid as the solvent and a large excess of concentrated hydrochloric acid as the isomerization medium.

In the improved process, the material to be isomerized, 5-fluoro-2-methyl-1-(p-methylthiobenzyl)-indenylidene-3-acetic acid is contacted in an anhydrous solvent, as for example, a halogenated hydrocarbon, with less than 1 mole of anhydrous hydrogen bromide per mole of reacting compound. The reaction may be carried out with or without a solvent; and when solvents are employed, solvents which are inert under the reaction conditions are used. Aromatic solvents such as benzene, and toluene, dioxane, dimethylformamide, triglyme, and other organic solvents may be employed. In fact, any solvent in which the indenylidene and hydrogen bromide are sufficiently soluble can be employed. In addition, halogenated hydrocarbons such as ethylene dichloride or halobenzenes may be used as solvents. The reaction medium actually preferred is one utilizing a halogenated hydrocarbon. It is especially preferred to use 1,2-dichloroethane, and from 10–50 mole percent of anhydrous hydrogen bromide based on the weight of the reacting species (0.1 to 0.5 moles anhydrous hydrogen bromide per mole of reacting indenylidene acetic acid). The amount of hydrogen bromide used is believed to be catalytic and large excesses may interfere with the production of the desired compound in high yield. It is therefore critical that the reaction be carried out within the molar range set forth hereinabove. When the reaction is carried out in the presence of anhydrous hydrogen bromide, it is stirred at a temperature between 50° and 100° C. in a sealed reaction vessel, maintained at a pressure of 10–15 pounds per square inch for a period of from 2–10 hours. Excellent yields are obtained when the reaction is conducted in the presence of approximately 25 mole percent hydrogen bromide and the reaction temperature is maintained at 75° C. for a period of 4–5 hours. The yield of product 5-fluoro-2-methyl-1-(p-methylthiobenzylidene)-indenyl-3-acetic acid, obtained by this method, is believed to be optimum and is greater than that described in any of the prior art patents.

The resulting p-methylthio compound, 5-fluoro-2-methyl-1-(p-methylthiobenzylidene)indenyl-3-acetic acid is then oxidized to the desired p-methylsulfinyl compound, 5-fluoro-2-methyl-1-(p-methylsulfinylbenzylidene)indenyl-3-acetic acid. The oxidation may be carried out by any number of standard techniques such as oxidation with $H_2O_2$, basic periodates or hypohalites, preferably the alkaline or alkaline earth periodates and hypohalites or organic peracids such as peracetic acid and monoperphthalic acid. Preferably, however, the oxidizing agent is $H_2O_2$. The reaction is preferably carried out in the presence of a solvent. For such purposes, $C_{1-5}$ alkanoic acids (acetic acid), halogenated hydrocarbons (chloroform), ethers (dioxane), $C_{1-5}$ alkanols (isopropanol) or mixtures thereof may be used.

The mole ratio of oxidizing agent to indene compound may be from 0.5 to 10, but preferably from 0.8 to 1.5. The reaction time and temperature are not critical, the reaction being carried out until substantial completion. Preferably, however, the time of reaction is from 1 to 18 hours and especially 2 to 6 hours at a temperature of 10° C. to 80° C. and especially 25° C. to 50° C.

In addition to the increased yield, substantial ecological advantages are gained by the unobvious method described in the present application. One such advantage is the reduction in the amount of acid used in the isomerization reaction. Thus, the prior art process uses a large excess of acetic acid as the solvent and concentrated hydrochloric acid as the aqueous acidic reactant. Following the reaction of the prior art, it was necessary to devise means of disposing of the large quantities of acetic and hydrochloric acids after isolation of the desired product. The present process utilizes only a small amount of anhydrous hydrogen bromide which is readily recovered by conversion to sodium bromide. The halogenated hydrocarbon, used as the inert liquid reaction diluent, is readily recovered by distillation and may then be reused in subsequent reactions.

The following example is intended to be illustrative rather than limitative of the invention disclosed herein.

EXAMPLE 1

5-Fluoro-2-methyl-1-(p-methylthiobenzylidene)-indenyl-3-acetic Acid

A suspension of 214 g. (0.63 mole) of 5-fluoro-2-methyl-1-(p-methylthiobenzyl)-indenylidene-3-acetic acid in 360 ml. of 1,2-dichloroethane and 13 g. (0.16 mole) of anhydrous hydrogen bromide is stirred in a sealed pressure reactor at 75° C. and 10–15 p.s.i. for 4–5 hours. The reactor is vented and the contents refluxed to remove excess hydrogen bromide. The mixture is cooled to -5° C. The batch is filtered and washed with cold 1,2-dichloroethane and dried to give 203 g. (95%) of product, m.p., 183°–185° C.

EXAMPLE 2

5-Fluoro-2-methyl-1-(p-methylsulfinylbenzylidene)indenyl-3-acetic Acid 34 g. (100 mmole) of the product from the preceding Example 1 is stirred in a mixture of 156 ml. of chloroform and 84 ml. of acetic acid under nitrogen, and the temperature is brought to 35° C. To this slurry is added 10.7 ml. of 9.6N aqueous $H_2O_2$ (30%) (103 mmole) over 1 minute. The temperature is maintained at 35° C. for a period of 4 hours. To the reaction mixture is then added 350 ml. of water, and the chloroform layer concentrated to a small volume in vacuo. The residue is crystallized from 260 ml. of ethanol, and the slurry aged 15 hours at 0.5° C. The product is filtered and washed with 60 ml. of 2BA ethanol, and dried in vacuo at 80° C. The product weighs 32.4 g. (91%); melting point, 183°–185° C.

Similarly, when sodium periodate or potassium hypochlorite is used in place of hydrogen peroxide, there is obtained the desired compound.

What is claimed is:

1. An improved process for the preparation of 5-fluoro-2-methyl-1-(p-methylsulfinylbenzylidene)-3-indenyl-acetic acid which comprises heating an anhydrous solution of 5-fluoro-2-methyl-1-(p-methylthiobenzyl)indenylidene-3-acetic acid in contact with anhydrous hydrogen bromide, wherein the molar ratio of 5-fluoro-2-methyl-1-(p-methylthiobenzyl)indenylidene-3-acetic acid to hydrogen bromide is between 1 to 0.1 and 1 to 0.5, and the temperature is maintained between 50°–100° C. in a sealed container, to produce 5-fluoro-2-methyl-1-(p-methylthiobenzyledene)indenyl-3-acetic acid, and submitting said indenyl-3-acetic acid to oxidation.

2. A process according to claim 1 wherein said anhydrous solution is 5-fluoro-2-methyl-1-(p-methylthiobenzyl)indenylidene-3-acetic acid dissolved in 1,2-dichloroethane in contact with anhydrous hydrogen bromide.

3. In an improved process for the preparation of 5-fluoro-2-methyl-1-(p-methylthiobenzylidene)-indenyl-3-acetic acid, the improvement which comprises heating an anhydrous solution of 5-fluoro-2-methyl-1-(p-methylthiobenzyl)indenylidene-3-acetic acid in contact with anhydrous hydrogen bromide, wherein the molar ratio of 5-fluoro-2-methyl-1-(p-methylthiobenzyl)-indenylidene-3-acetic acid to hydrogen bromide is between 1 to 0.1 and 1 to 0.5, and the temperature is maintained between 50°–100° C. in a sealed container.

4. A process according to claim 3 in which the anhydrous solution is 5-fluoro-2-methyl-1-(p-methylthiobenzyl)indenylidene-3-acetic acid dissolved in 1,2-dichloroethane.